United States Patent [19]
Schramm

[11] 4,014,109
[45] Mar. 29, 1977

[54] TEST APPARATUS FOR NUCLEAR IMAGING DEVICES

[75] Inventor: Douglas Schramm, Winfield, Ill.

[73] Assignee: Anasim, Inc., Aurora, Ill.

[22] Filed: Feb. 12, 1975

[21] Appl. No.: 549,166

[52] U.S. Cl. .................................. 35/17; 250/510
[51] Int. Cl.² .................. G09B 23/28; G21K 3/00
[58] Field of Search ...................... 35/17; 250/510

[56] References Cited

UNITED STATES PATENTS

| | | | |
|---|---|---|---|
| 1,953,249 | 4/1934 | Michel | 250/510 |
| 3,010,223 | 11/1961 | Alderson | 35/17 |
| 3,348,319 | 10/1967 | Harrison | 35/17 X |
| 3,487,559 | 1/1970 | Freedman | 35/17 |

FOREIGN PATENTS OR APPLICATIONS

| | | | |
|---|---|---|---|
| 39,636 | 6/1957 | Poland | 250/510 |

Primary Examiner—Harland S. Skogquist
Attorney, Agent, or Firm—Leydig, Voit, Osann, Mayer & Holt, Ltd.

[57] ABSTRACT

A single test phantom for evaluating the scan of a nuclear imaging device is provided which comprises a container having a sealed cavity therein, the outer walls simulating the outline of a human organ or a portion of the body which can be scanned. A means to allow injection of a suitable radioisotope into the cavity is provided, as are a plurality of radioisotope-collecting areas of various sizes and depths which simulate the various conditions that would be seen in a typical scan. By comparing the scan of the test phantom to the test phantom itself, the physician via the single scan can determine whether the nuclear imaging device being tested is properly calibrated and is in satisfactory operating order in an environment simulating an actual scan of a patient.

7 Claims, 3 Drawing Figures

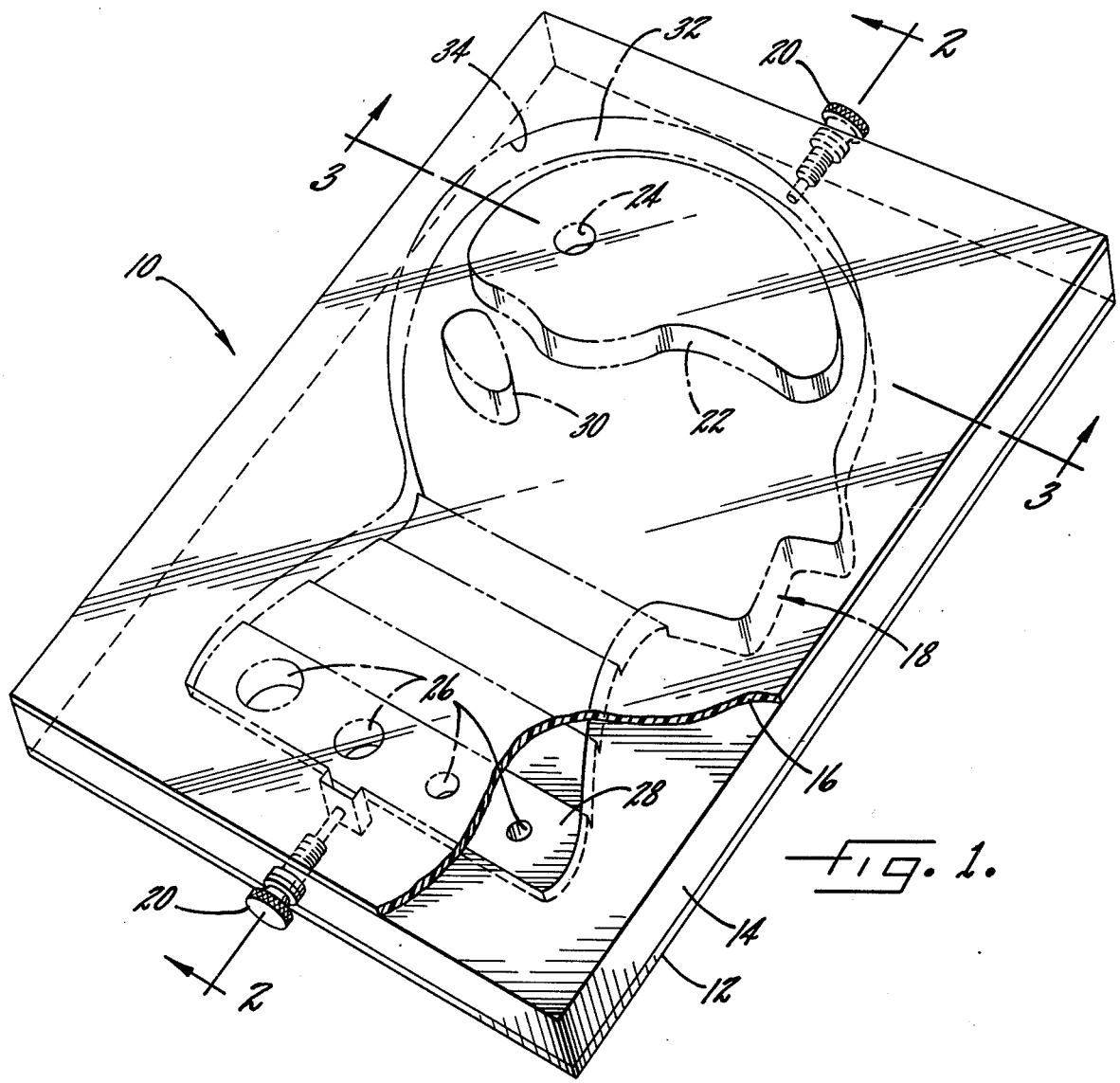
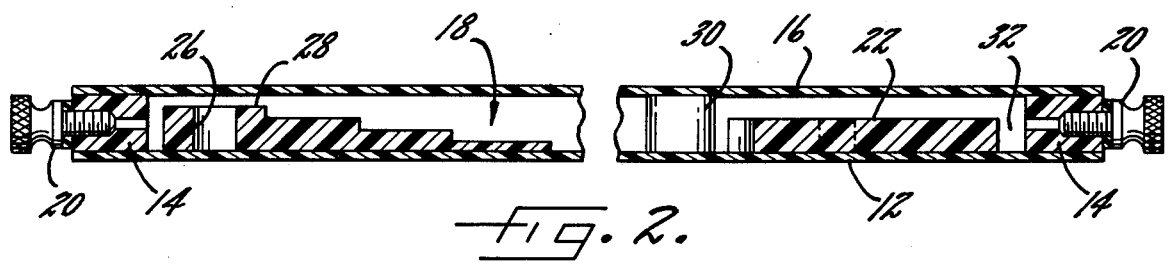
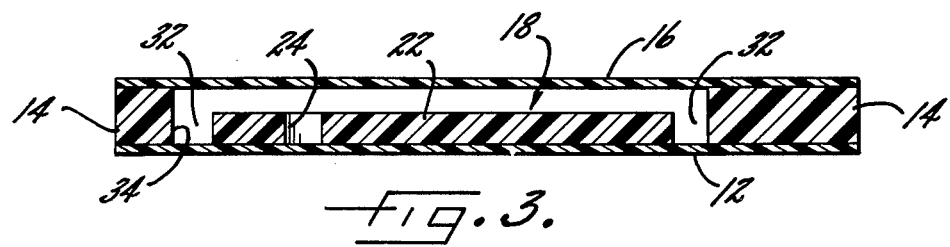

TEST APPARATUS FOR NUCLEAR IMAGING DEVICES

This invention relates to scintigraphy and, more particularly, to test apparatus for nuclear imaging devices such as a rectilinear scanner or scintillation camera.

The use of rectilinear scanners or cameras in various clinical applications is well known. As an example, in brain scintigraphy, the blood brain interface in the normal person is an effective barrier for many substances, among them the radioisotopes used for brain scintigraphy. In a normal brain scan, the radioactivity will be deposited in the sagittal and transverse sinuses. Practically any kind of disease will alter the permeability of the blood brain barrier and will permit the accumulation of certain substances, such as radioisotopes, in the diseased areas. Thus, diseases such as encephalitis, multiple sclerosis, tumors, vascular accidents and the like result in an increased accumulation of the radioisotope in the diseased area. It is generally conceded that brain tumors, abscesses and most vascular abnormalities result in increased permeability of the normal brain to the isotope. Since the radioisotope, when injected intravenously, concentrates in these abnormal areas, the above conditions result in increased radioactivity, thereby giving a "hot spot" on the scan and/or direct information regarding the existence, size and location of the abnormality. This localization is particularly helpful to the neurosurgeon as it aids him in deciding the location and size for a bone flap in his surgical approach. Further, this also aids the radiologist in planning therapeutic irradiation.

Proper calibration of the apparatus used to make the scan as well as the proper functioning of the components such as the photomultipliers used in the apparatus is obviously crucial in assuring that the scan which is made accurately represents the condition of the patient being examined. The manufacturers of this type of equipment have developed sophisticated test equipment that has minimized this problem to some extent.

However, the utilization of this test equipment does not provide a complete answer to the problem. The technician using the rectilinear scanner or the like will typically neither have test equipment of this type at his disposal nor will generally have the background necessary to allow him to properly check both the calibration and the functioning of the components of the equipment. It would accordingly be highly desirable for the technician using the rectilinear scanners to have a ready means of testing the scanner prior to usage so as to insure that the scans to be made will be accurate.

An attempt to provide such a means is presently commercially available. This means comprises a series of reference phantoms that are proposed to be used for checking the performance of such scanners. A series of three phantoms is said to simulate clinical conditions and allows checking of the three most impotant parameters of the performance of a scintillation camera or scanner, viz. — depth-resolution, uniformity of response and sensitivity.

Considering such means in greater detail, the Hine Reference Phantom can be filled with a solution of a radionuclide chosen according to the application for which the equipment is being tested, typically Iodine-131 or Technetium-99m, and consists of four concentric rings, each one inch wide, around a central one inch well. The depths of the successive rings increase so that the intensity of the gamma rays emitted from each ring increases in about five equal steps from the outer ring towards the center well. The more clearly the five steps are displayed, the better the resolution of the instrument.

The Flood Phantom consists of a square plastic form having a circular cavity. A solution containing the desired radioisotope may be placed in the cavity via a filling port. When the radioactivity is distributed uniformly throughout the phantom, as by shaking vigorously, the scintillation camera's uniformity of response can be determined.

The Bar Phantom consists of four sets of lead bars of varying dimensions which are embedded in a holder. This is considered as a means of checking the intrinsic resolution, collimator spatial resolution, field size and linearity of the equipment.

In addition, a brain scanning phantom is commercially available which accurately simulates the normal brain study obtained from gamma scintillation cameras and rectilinear scanners. Such phantoms are made of clear plastic sheets which sandwich a filter-paper mask that has been impregnated with various concentrations of $^{57}Co$. The configuration is said to faithfully reproduce the distribution of $^{99m}Tc$ in the normal brain. A simulated tumor, a filter paper saturated with $^{57}Co$, can be placed anywhere on the phantom surface so as to demonstrate possible tumor locations and the masking of tumors by the normal distribution of $^{99m}Tc$ in the brain.

While using such phantoms may be satisfactory to test the reliability of the various nuclear imaging devices this does not provide a unitary means of coordinating the various aspects of the equipment to an actual brain scan which the physician must read. Stated another way, such phantoms do not provide the physician with a method of evaluating the performance of a nuclear imaging device which utilizes a means that is directly correlative to an actual scan.

It is accordingly a principal object of the present invention to provide a single test phantom which simulates the response that would be obtained by an actual scan using a nuclear imaging device.

A further object provides a single test phantom which allows a determination of both the proper operation of such nuclear imaging devices as well as calibration check of such equipment.

Another object lies in the provision of a test phantom which can be readily employed by the technicians operating nuclear imaging devices.

A still further and more specific object of this invention is to provide a single test phantom which allows the extent of resolution for a particular nuclear imaging device to be determined.

Yet another object provides a test phantom that enables a technician to utilize the proper scanning techniques for a particular nuclear imaging device.

Another object lies in the provision of a test phantom which enable the counting rates, time constant, suppression and densities of a particular nuclear imaging device to be properly evaluated.

Other objects and advantages of the present invention will become apparent in view of the following description, taken in conjunction with the accompanying drawings, in which:

FIG. 1 is a perspective view of the single, test phantom of the present invention, partially cut away;

FIG. 2 is a cross-sectional view, taken generally along line 2—2 of FIG. 1 and generally illustrates the various layers forming the test phantom; and FIG. 3 is a cross-sectional view taken generally along lines 3—3 of FIG. 1 and shows a medium radioisotope density regions which simulates an area on a scan substantially equivalent to that of the human brain as well as the region of high radioisotope density.

While the invention will be described in connection with certain preferred embodiments, it will be understood that it is not intended to limit the invention to these embodiments. On the contrary, it is intended to cover all alternatives, modifications and equivalents as can be included within the spirit and scope of the invention as defined in the appended claims. For example, while the illustrated test phantom is in the shape of the head and human brain, it should be appreciated that the shape of other organs of a human body could also be used. The configuration for the phantom selected may similarly be employed to evaluate the performance of the nuclear imaging apparatus being used, regardless of which body organ is to be scanned. The important aspect is that the phantom embody regions of varying radioisotope density so that the physician evaluating a scan of the test phantom can evaluate these regions in a simulation of some type or organ. However, it is particularly preferred to employ the illustrative embodiment as brain scans are considered to be the most difficult to evaluate; and the illustrative embodiment provides a directly correlative testing tool.

Thus, the present invention provides a single test phantom having a cavity in the outline of a human organ or a portion of the body which can be scanned, a means for allowing the injection of a suitable radioisotope into the cavity and a plurality of radioisotope-collecting areas of various sizes and depths which simulate the various conditions that would be seen in a typical scan. By comparing the scan of the test phantom to the test phantom itself, the physician via the single scan can readily determine whether the rectilinear scanner or the like is properly calibrated and is in satisfactory operating order in an environment simulating an actual scan of a patient.

Turning now to the drawings, there is shown in FIG. 1 a perspective view of a test phantom 10 in accordance with the present invention. The test phantom 10 comprises, as can be seen from FIGS. 1 and 2, a bottom layer 12, a central layer 14 and a top layer 16 joined together to form a unitary container by any suitable means (not shown) such as any conventional adhesive. Various epoxy resins have been found to be suitable. Desirably, for aesthetic purposes, the top layer 16 is formed from a transparent material; and the central layer 14 and the bottom layer 12 have contrasting colors. However, neither of these aspects are certainly essential. The various layers may be formed from any material which can tolerate whatever radioisotope that is used and which has sufficient rigidity so that the test phantom itself does not bend to any significant extent. Also, the container, while conventionally comprised of three layers, may suitably be made from a single piece of material or may comprise two layers.

As best seen in FIG. 1, the test phantom 10 has a cavity 18 which simulates, in this illustrative embodiment, the outline of a human head. The depth of the cavity 18 may be varied as desired; however, it has been found suitable to employ a depth in the range of about ½ of an inch or so. To allow injection into the cavity of whatever radioisotope is to be used, any conventional means can suitably be utilized. As shown, threaded rubber stoppers 20 serve as closures for the access orifices through which the desired radioisotope can be injected into the cavity 18, as with a syringe. The location of the rubber stoppers, or other means used for allowing injection of the radioisotope, can be varied as desired. Such means should, of course, be designed to prevent leakage of the radioisotope once the cavity has been appropriately filled. Desirably, more than one access orifice is provided so that one orifice can function as a venting means. Alternatively, any other conventional venting means may be utilized, if desired.

To provide an area allowing simulation of normal accumulation of radioisotope in the human brain, a first insert 22 in the general outline of the human brain is provided and is located in the typical spatial relationship to the outline of the head. The depth of the first insert 22 in relation to the depth of the cavity 18 should be such as to provide this simulation. It has been found desirable to maintain the depth of the first insert 22 at approximately 50 to 70% of the overall depth of the cavity 18. Suitably, the relative depth of the first insert 22 is such that a scan of this area will show up as the lightest shaded area discernible.

The simulation of a tumor (or any other disease which would provide for a high zone of radioisotope concentration) is provided by the void 24 in the first insert 22, which, as illustrated, extends the entire depth of the cavity 18. It is not essential that the void 24 have a depth equivalent to that of the cavity 18; all that is required is a depth sufficient to provide a shade on the scan that is discernible from the scan shade imparted by the first insert 22. The size and location of the void 24 can be varied as desired. However, it is preferred to locate the void 24 sufficiently close to the edge of the first insert 22 so that the shade contrast on the scan can be readily valuated. Further, the size and shape of the void 24 desirably approximates that of an average tumor or the like.

In accordance with one aspect of this invention, a series of voids of varying sizes may be provided. To this end, and as seen in FIG. 1, a series of voids, generally designated at 26, are included adjacent the bottom of the phantom, cut out from a contrast insert 28. Desirably, the size of the voids increases from a minimum approximating the smallest size area that a nuclear imaging device can detect in a scan up to a size significantly in excess of that minimum, typically several times that of the minimum. While the specific sizes may be varied as desired, the illustrative series of the circle voids ranges from a minimum of 0.25 cm. diameter to 2.0 cm. maximum. It should, of course, be appreciated that the location and geometrical shape of this series of voids can be varied as desired. Indeed, if preferred, the series may be located within the first insert 22 and void 24 may be part of the series. The depth of the voids need not be equal to the depth of the cavity 18 but may be varied as described in connection with void 24.

A zone of minimal radioisotope concentration is provided by a second insert 30 which extends essentially the full depth of the cavity 18 so that the area on the scan will appear as substantially white. The positioning of the second inserts 30 in the cavity is not particularly critical. It is however preferred to locate this insert so that a direct contrast on the scan between the substantially white area imparted by the second insert and the light shade provided by the first insert can be evaluated as well as the contrast with the dark area imparted by the void 24. If desired, a number of such second inserts can be provided.

In accordance with a further aspect of the present invention, the channel 32 between the first insert 22 and the outline of the test phantom, as shown at 34, should vary gradually and provide an area therebetween which is no more than about ½ inch in width so as to aid in evaluating the resolution of the equipment.

In use, to test the nuclear imaging device such as the rectilinear scanner or the like that is being used, the technician can simply take, after filling of the cavity 18 with the desired radioisotope, one scan of the test phantom and then compare this scan to the actual phantom itself. If the equipment is either malfunctioning or the calibration is improper, this can be readily ascertained by the visual comparison. A measured comparison of the various areas on the test scan with the sizes of the areas on the test phantom can also be made to accurately check the calibration of the nuclear imaging device. In this regard, if desired, the test phantom may also include a series of rectangular shaped voids with varying widths to further check the calibration.

Thus, as has been seen, the present invention provides a single test phantom which can be readily manufactured and which is capable of insuring that a nuclear imaging device such as a rectilinear scanner or the like is operating properly and is accurately calibrated without the need for sophisticated test equipment. An accurate simulation of the responses that would be obtained through an actual scan are provided.

I claim as my invention:

1. A test phantom for evaluating the scan of a nuclear imaging device which comprises a container having a sealed cavity therein, the outer walls simulating the outline of a human head and the cavity having a predetermined depth, a means for allowing injection of a radioisotope into the cavity, a first insert located in said cavity and at least substantially simulating the shape and location of the human brain, said first insert having a depth simulating, after addition of the radioisotope to fill the cavity and on a scan of the test phantom, an area discernible on the scan substantially equivalent to the human brain, a second insert located adjacent the first insert and having a depth substantially equal to that of the cavity and simulating on a scan an area which is substantially white and said first insert having at least a partial void located therein simulating on a scan an area discernible from the remainder of said first insert.

2. The test phantom of claim 1 wherein the void in said first insert is located adjacent said second inert.

3. The test phantom of claim 1 which includes a means for venting the cavity.

4. The test phantom of claim 1 wherein the void in said first insert has a depth substantially equal to the depth of the cavity.

5. The test phantom of claim 1 wherein the depth of said first insert is in the range of from about 50 to about 70% of the depth of the cavity.

6. The test phantom of claim 1 which includes a series of voids located in the cavity and having sizes ranging from the minimum size capable of being detected on a scan of the test phantom by the nucelar imaging device to a maximum significantly in excess of said minimum.

7. A test phantom for evaluating the scan of a nuclear imaging device which comprises a container having a sealed cavity therein, the outer walls of the cavity simulating a portion of the body and the cavity having a predetermined depth, a means for allowing injection of a radioisotope into the cavity, a first insert located in said cavity and spaced from the cavity walls and having a thickness in relation to the cavity thickness which simulates, after addition of rdioisotope to fill the cavity and on a scan of the test phantom, the lightest shade discernible, a second insert located adjacent the first insert and having a depth substantially equal to that of the cavity and simulating on a scan an area which is substantially white and said first insert having at least a partial void located therein simulating on a scan an area discernible from the remainder of said first insert.

* * * * *